US007312355B2

(12) United States Patent
Corma Canòs et al.

(10) Patent No.: US 7,312,355 B2
(45) Date of Patent: Dec. 25, 2007

(54) METHOD OF PREPARING FATTY ACID MONOESTERS

(75) Inventors: Avelino Corma Canòs, Valencia (ES); Sara Iborra Chornet, Valencia (ES); Alexandra Isabelle Velty, Valencia (ES); Sharifah Bee Abd Hamid, Kuala Lumpur (MY)

(73) Assignees: Consejo Superior de Investigaciones Cientificas, Madrid (ES); Universidad Politecnica de Valencia, Valencia (ES); Universiti Malaya, Kuala Lumpur (MY)

(*) Notice: Subject to any disclaimer, the term of this patent is extended or adjusted under 35 U.S.C. 154(b) by 0 days.

(21) Appl. No.: 11/403,142

(22) Filed: Apr. 12, 2006

(65) Prior Publication Data

US 2007/0037994 A1    Feb. 15, 2007

Related U.S. Application Data

(63) Continuation of application No. PCT/ES2004/070084, filed on Oct. 14, 2004.

(30) Foreign Application Priority Data

Oct. 14, 2003    (ES) ................................ 200302467

(51) Int. Cl.
*C07C 67/02*    (2006.01)

(52) U.S. Cl. ...................................... 560/217; 560/234

(58) Field of Classification Search ................ 560/231, 560/234; 554/167, 168, 169
See application file for complete search history.

(56) References Cited

U.S. PATENT DOCUMENTS

| 4,032,550 A | 6/1977 | White et al. |
| 6,090,959 A | 7/2000 | Hirano et al. |

FOREIGN PATENT DOCUMENTS

| ES | 2124166 | * | 1/1999 |
| FR | 2745296 | | 8/1997 |
| FR | 2794768 | | 12/2000 |
| WO | 199856747 | * | 12/1998 |

OTHER PUBLICATIONS

Barrault et al. Catalysis Today, vol. 75, Issues 1-4 , Jul. 3, 2002, pp. 177-181.*

* cited by examiner

*Primary Examiner*—Karl Puttlitz
(74) *Attorney, Agent, or Firm*—Klauber & Jackson L.L.C.

(57) ABSTRACT

The invention relates to a method of producing fatty acid monoesters and polyhydroxylic alcohols by means of transesterification between a polyhydroxylic alcohol and a compound that is selected from a fat of animal origin, a fat of vegetable origin, and a fatty acid methyl ester. The invention is characterised in that the transesterification reaction is performed in the presence of basic solid catalysts, said basic solids being oxides that are selected from mixed oxides of one or more monovalent metals and one or more trivalent metals, mixed oxides of one or more divalent metals and one or more trivalent metals, and mixtures of same.

13 Claims, No Drawings

METHOD OF PREPARING FATTY ACID MONOESTERS

RELATED APPLICATIONS

The present application is a continuation of co-pending PCT Application No.PCT/ES2004/070084, filed on Oct. 14, 2004, which in turn, claims priority from Spanish Application Ser. No. 200302467, filed on Oct. 14, 2003. Applicants claim the benefits of 35 USC §§120 and 111 as to the PCT application, and priority under 35 USC §119 as to the said Spanish Application, and the entire disclosures of both applications are incorporated herein in their entireties.

FIELD OF THE TECHNIQUE

Preparation of fatty acid monoesters and of polyhydroxylic alcohols by transesterification between a polyhydroxylic alcohol and a fat or fatty acid methyl ester.

BACKGROUND

The mono- and diesters of fatty acids and polyhydroxylic alcohols, particularly glycerin, are compounds extensively utilized as emulsifying and surface-active agents in the food, cosmetic and pharmaceutical industries. These compounds can be obtained in two different ways: A) by direct esterification between the fatty acid and the polyhydroxylic alcohol; B) by transesterification between a polyhydroxylic alcohol and a fat (triglyceride) or a fatty acid methyl ester. From the industrial point of view, the transesterification processes are the most important for the preparation of mono- and diesters of fatty acids and polyols.

Transesterification is a reaction which takes place, as is indicated in the schematic, between an ester (1) and an alcohol (2) giving rise to a new ester (3) and another alcohol (4).

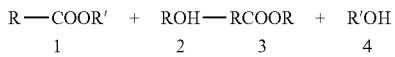

In general transesterifications can be catalyzed by both acids and bases. However, in many cases the use of basic catalysts is preferable, since acid catalysts can cause, depending on the structure of the alcohols which intervene in the process, secondary reactions such as isomerizations or dehydrations.

In transesterification catalyzed by bases the preferred catalysts are conventional bases such as KOH, NaOH, alkaline alkoxides such as $NaOC_2H_5$, $NaO\text{-}t\text{-}C_4H_9$, or $NaHCO_3$, $Na_2CO_3$, and $Ca(OH)_2$. This type of catalyst is difficult to eliminate from the end product and in addition they are not reusable.

C. M. Gooding et al., H. W. in the patent U.S. Pat. No. 2,197,339, describe a method for the transesterification of coconut oil with glycerin using $NaHCO_3$ and $Na_2CO_3$ as catalysts. They obtain a mixture of esters and salts of fatty acids which are then made to react with different chlorohydrins like for example chlorohydrin of glycerol, giving rise to the formation of a monoester and NaCl.

Montañola Martinez et al., describe in the Spanish patent application P-9001084 "Procedure for the preparation of fatty acid monoesters with glycols", assigned to Kao Corporation, a method for the transesterification of esters of fatty acids with glycerin using dry $Na_2CO_3$ as catalyst.

Also in the European patent EP-0200982 (Henkel) the transesterification of triglycerides with alcohols is described at temperatures of between 60-75° C. and atmospheric pressure in the presence of $Na_2CO_3$ or $NaHCO_3$.

In the patent EP-1260497 (2002), a process is described for obtaining monoesters of polyhydroxylic alcohols with high yields and purity. The transesterification between vegetable oils and polyols is performed in the presence of a solvent (tert-butanol or tert-amyl alcohol) at temperatures of between 160 and 200° C. and using base catalysts such as salts (oxides, hydroxides, carbonates, alkoxides and acetates) of alkaline and alkaline-earth metals and nitrogenated bases.

The transesterification processes presented above have serious drawbacks, like for example the use of solvents that have to be completely removed from the end product, or the use of homogeneous basic catalysts that must be neutralized and the resulting salts eliminated from the reaction medium, as well as the impossibility of reusing the catalyst.

The use of heterogeneous basic catalysts greatly simplifies this type of process. The heterogeneous basic catalyst is easily eliminated from the reaction medium by filtration, it allows the possibility of reuse and its application is also possible in fixed bed processes.

Corma et al., describe the use of heterogeneous basic catalysts of the type of alkaline-earth metal oxides, calcinated hydrotalcites, zeolites, sepiolites and zeotypes exchanged with alkaline cations as catalysts in the transesterification of mono—or polyhydroxylic alcohols with fats of animal or vegetable origin (Spanish patent application P9601087; Journal Catalysis 173, 315 (1998)). The transesterification of glycerin with methyl esters of fatty acids has also been performed using solid catalysts with a basic nature. Barrauti et al., describe the transesterification of methyl esters with glycerol in the presence of oxides such as MgO, $CeO_2$ and $La_2O_3$, as well as MgO doped with alkaline metals (Li/MgO and Na/MgO) (Applied Catalysis A, 218, 1 (2001); Catalysis Today 75, 177 (2002)).

The present invention refers to a procedure for transesterification between polyhydroxylic alcohols and fatty esters, preferably triglycerides and methyl esters, using heterogeneous basic catalysts based on combinations of mono- and trivalent metal oxides and in combinations of di- and trivalent hydrated metal oxides.

With this type of mixed oxide higher reaction speeds and better selectivities to monoesters are achieved than with those known up to now, formed by a mixed oxide of a monovalent metal and a divalent metal which, in principle, would seem more suitable to carry out the transesterification according to its basicity.

It has been proven and described also that for a transesterification process, more active catalysts are obtained than the conventional mixed oxides formed by mixed oxides of divalent and trivalent metals, if these are rehydrated with a determined quantity of water.

DESCRIPTION OF THE INVENTION

The present invention refers to a procedure for obtaining fatty acid monoesters and polyhydroxylic alcohols by transesterification between a polyhydroxylic alcohol and a compound selected from a fat of animal origin, a fat of vegetable origin and a fatty acid methyl ester, characterised in that it is performed in the presence of basic solid catalysts, said basic solids being oxides selected from mixed oxides of one or more monovalent metals and one or more trivalent metals, mixed oxides of one or more divalent metals and one or more trivalent metals, and mixtures of same.

In accordance with a preferred embodiment of the procedure, the catalyst comprises mixed oxides of one or more trivalent metals $M^{III}$, and one or more monovalent metals $M^I$, and mixtures of same, for which the ratio $M^I/M^{III}$ is between 2 and 4. Preferably in said embodiment, said trivalent metal is selected from Ga, Al, Fe, B, Ce, La and mixtures of same.

Preferably in said embodiment said monovalent metal is selected from Li, Na, K, Rb, Cs, and mixtures of same.

In accordance with an additional embodiment of the procedure, the catalyst is selected from among one or more hydrated mixed oxides of one or more trivalent metals and one or more divalent metals $M^{II}$, and mixtures of same, with a ratio $M^{II}/M^{III}$ of between 2 and 5, the water content of these hydrated mixed oxides being preferably between 15 and 80% by weight with respect to the precursor mixed oxide. Preferably said trivalent metal is selected from Ga, Al, Fe, Ce, La and mixtures of same. Preferably said divalent metal is selected from Mg, Zn, Co, Ni, Ca, Cu, Mn and mixtures of same. According to this embodiment, the mixed oxide of these characteristics undergoes a process of rehydration prior to its use as a basic catalyst. The rehydration is performed by subjecting the mixed oxide to a nitrogen current saturated with water vapor or adding the quantity of water directly to the mixed oxide. The content in water of these mixed rehydrated oxides is preferably comprised between 15 and 80% by weight with respect to the precursor mixed oxide.

In the procedure of the present invention the catalyst, according to a preferred embodiment, can be alumina impregnated with salts which, after its calcination, produces the corresponding oxide supported on the alumina and in which the percentage of the impregnated salt is between 1 and 40%, preferably between 1 and 20%. In a preferred manner, the calcination of these salts is performed with air and/or nitrogen, free of $CO_2$. In a preferred manner said impregnated salts are selected from organic salts, nitrates, carbonates and hydroxides, and they are preferably salts of alkaline metals selected from Li, Na, K, Rb, Cs and mixtures of same.

According to additional preferred embodiments said catalyst is a mixed oxide selected from mixed oxide of aluminium and magnesium, mixed oxide of aluminium and lithium, and lithium oxide impregnated on gamma-alumina.

For the transesterification reaction in the procedure of the present invention, the fats are preferably triglycerides.

The triglycerides can be of animal or vegetable origin, such as fish oil, coconut oil, palm oil, corn oil, olive oil, soya oil and rapeseed oil.

The methyl esters are esters of fatty acids, saturated or unsaturated, which contain preferably between 10 and 32 carbon atoms.

The polyhydroxylic alcohols are for example glycerol, sorbitol, mannitol, xylitol, polyethylene glycols, etc.

The heterogeneous basic catalysts according to the present invention are solids of high surface area and they produce monoesters of polyalcohols with high yield and selectivity.

The transesterification reaction takes place according to conventional procedures in a continuous or discontinuous reactor of the stirred tank type or in a continuous reactor with fixed or fluidized bed in which the catalyst is located.

The transesterification reaction is performed preferably in a temperature range of between 50 and 260° C., more preferably between 150 and 250° C. using a proportional weight of polyol to ester preferably between 0.2 and 20, more preferably between 1 and 10, the quantity of catalyst used being between 0.1 and 10%, more preferably between 1 and 6% with respect to the total weight of reagents.

According to the invention, the reaction is performed in the presence of air or in an inert atmosphere, at a pressure selected from atmospheric pressure, reduced pressure of between 10 and 100 mmHg, more preferably between 15 and 50 mmHg and in a reactor at a pressure of between 2 and 100 atm., more preferably between 10 and 50 atm.

EXAMPLES

Example 1

Preparation of a Mixed Oxide Formed by a Monovalent and a Trivalent Metal: Preparation of a Mixed Oxide of Al—Li A solution of 17% by weight of aluminium tri-sec-butoxide in hexane is added drop by drop to an aqueous solution of lithium carbonate (0.55% m/m) with vigorous stirring at ambient temperature. The resulting suspension is heated in autoclave to 60° C. for 24 h. When this time has elapsed, the resulting solid is filtered and rinsed until the pH of the rinsing water is equal to 7. Next and after drying the solid at 60° C. for 12 h, it is calcinated at 450° C. for 8 h.

Example 2

Preparation of a Mixed Oxide of a Hydrated Divalent Metal and a Hydrated Trivalent Metal: Preparation of a Mixed Oxide of Al—Mg (Mg/Al=4), Hydrated to 43%

The mixed oxide of Al—Mg is prepared by mixing two solutions: A and B. Solution A contains (3–x) moles of $Mg(NO_3)_2.6H_2O$ and x moles of $Al(NO_3)_3.9H_2O$ in distilled water, the solution being 1.5 M in (Mg +Al) and the Mg/Al ratio=4. The B solution is prepared by dissolving (6+x) moles of NaOH and 2 moles of $Na_2CO_3$ in the same volume of distilled water as the A solution. The two solutions A and B are mixed at a rate of 1 mL/min under vigorous mechanical stirring at ambient temperature. The resulting gel is heated in autoclave at 60° C. for 12 hours. After this time the resulting solid is filtered and rinsed repeatedly with water until the pH of the rinsing water is 7. After drying the solid at 80° C. for 12 h, it is calcinated at 450° C. for 8 h under a nitrogen current free of $CO_2$. The mixed oxide so obtained is hydrated in a nitrogen current (40mL/min) saturated with water vapor and free of $CO_2$ for the time necessary to obtain a water content of 43%.

Example 3

Preparation of a Monovalent Metal Oxide on a Trivalent Metal Oxide: Preparation of an Oxide of Li on $Al_2O_3$ from $LiNO_3$ Supported on Gamma-alumina A solution of 0.18 g of $LiNO_3$ solved in 50 ml of methanol is added with 3 g of gamma-alumina. The suspension is subjected to magnetic agitation at a temperature of 50° C. during 3 hours. When this time has elapsed, methanol is evaporated in a rotary evaporator and the resulting solid is dried at 60° C. during 12 hours, after which it is calcinated at 500° C. in presence of air free of $CO_2$.

Example 4

Transesterification of Glycerol with Rapeseed Oil

The glycerine and rapeseed oil are added in a two-mouth flask with refrigerant having a glycerine/oil relation weight of 0.62. The system is heated at atmospheric pressure to a temperature of 240° C. adding a 4% in weight of the heterogeneous catalyst. After 5 hours of reaction the catalyst is strained and the surplus glycerine is separated by decanting or by extraction of the fatty phase with hexane. The crude is analysed by gas chromatography after silanization of the specimen. Table 1 shows the results obtained with the mixed oxide of Li—Al (LiAl (0) and a rehydrated mixed oxide of Al—Mg (MgAl(O)—R) having a 43% water content in accordance with examples 1 and 2 respectively. These results are compared with the ones obtained when the reaction is performed without catalyst and when a conventional basic oxide is used like the MgO that has been described in Corma et al., in the Spanish patent application mentioned in the background chapter P9601087; and in the above mentioned references Journal Catalysis 173, 315 (1998)), Barrault et al. (Applied Catalysis A, 218, 1 (2001); Catalysis Today 75, 177 (2002) and EP-1260497.

TABLE 1

| Catalyst | ro ($10^3$) Molmin$^{-1}$g$^{-1}$ | Conversion (%) | Output (%) Mono | Di- | AO[b] | Selectivity to monoglycerides (%) |
|---|---|---|---|---|---|---|
| Without catalyst | — | 38 (8 h) | 17 | 18 | 3 | 44 |
| MgAl(O)R | 0.35 | 100 (3 h)[a] | 87 | 11 | 2 | 87 |
| LiAl(O) | 1.7 | 100 (1 h)[a] | 80 | 16 | 4 | 80 |
| MgO | 0.65 | 100 (1 h)[a] | 74 | 24 | 2 | 74 |

Results of the glycerolysis of the rapeseed oil in presence of different basic catalysts. Reaction conditions: glycerol/rapeseed oil molar relation of ~6, 4% in weight of catalyst with regard to total reaction mass, at 240° C. [a] the reaction time at which the maximum selectivity is reached. [b] Oleic Acid.

It is observed from the results how the hydrated mixed oxide of Al—Mg, even having a smaller initial reaction speed (activity) produces monoglycerides with a high selectivity. In addition, the catalyst formed by an oxide of a monovalent and trivalent metal, in this specific case by a mixed Li and Al oxide is very active (see the initial speed (ro) and very selective at monoglyceride and in any case more selective than a conventional magnesium oxide catalyst.

Example 5

Reuse of Al—Mg Hydrated Mixed Oxide

The transesterification reaction between the glycerine and rapeseed oil is performed as described in example 4 using a glycerine/rapeseed oil relation in weight equal to 1 in presence of a mixed Al—Mg hydrated oxide with a 43% water content. After the reaction, the catalyst was filtered and washed repeatedly with methanol. The same catalyst was reused in a second, third, fourth and fifth cycle. Table 2 shows the results obtained in each of the reuses.

TABLE 2

Reuse of MgAl(O)—R[a]

| Cycles | Conversion of Rapeseed Oil (%) (2 h) | Output in monoesters (%) | Selectivity to monoesters (%) |
|---|---|---|---|
| 1 | 100 | 92 | 92 |
| 2 | 100 | 89 | 89 |
| 3 | 100 | 93 | 93 |
| 4 | 100 | 93 | 93 |

[a]Reaction conditions: Glycerol/AC = 10 molar relation, 4% of catalyst at 240° C.

Example 6

Transesterification of the Methyl Oleate with Glycerine

The glycerine and methyl oleate are added in a two-mouth flask with a refrigerant in a molar relation glycerine/ester of 6. The system is heated at atmospheric pressure to a temperature of 200° C. and a 4% in weight of the heterogeneous catalyst is then added. A Dean-Stark device coupled to the reaction system permits the displacement of the methanol formed during the reaction. Table 3 show the results obtained using a mixed Li—Al (LiAl(O)) oxide and a mixed hydrated Al—Mg oxide with a 24% of water (MgAl(O)—R).

TABLE 3

| Catalyst | Conversion MeO/% | Output (%) Monoester | Diester | Selectivity to monoesters (%) |
|---|---|---|---|---|
| Al—Mg (=)—R[c] | 92[b] | 81 | 11 | 88 |
| LiAl(O) | 96[a] | 80 | 16 | 82 |

Results of the transesterification of the methyl oleate in presence of basic catalysts. Reaction conditions: glycerol/OMe molar relation of ~6, 4% in weight of catalyst with regard to total mass of reactives, 200° C.
[a]6 h of reaction;
[b]8 h of reaction;
[c]24% water content.

Example 7

Transesterification of the Methyl Oleate with Glycerine using a Catalyst Based on LiNO$_3$, Supported on Gamma-alumina as Described in Example 3

The transesterification reaction between the methol oleate and the glycerine is performed as shown in example 6 at a temperature of 220° C., using as basic heterogeneous catalyst gamma-alumna impregnated with different percentages of LiNO$_3$, and later calcinated at 500° C. Table 4 shows the results obtained with these catalysts.

TABLE 4

| Catalyst | Time (h) | Output (%) Monoester | Diester | Selectivity to monoesters (%) |
|---|---|---|---|---|
| Li-Alumina (1%)[a] | 24 | 80 | 10 | 88 |
| Li-Alumina (3%)[a] | 4 | 80 | 20 | 80 |
| Li-Alumina (6%)[a] | 2 | 80 | 20 | 80 |

[a]Impregnation percentage in Li

Example 8

Transesterification of Other Methyl Esters of Fatty Acids with Glycerol in Presence of a Li—Al Mixed Oxide as Described in Example 1

The transesterification of the methyl palmitate and laurate was performed in accordance with example 6 at a temperature of 220° C. using as basic heterogeneous catalyst a mixed oxide of Li and Al. Table 5 shows the transesterification results of these esters.

TABLE 5

| Methyl Ester | Time (h) | Output (%) Monoester | Diester | Selectivity to monoesters (%) |
|---|---|---|---|---|
| Laurate | 1 | 89 | 11 | 89 |
| Palmitate | 1.5 | 75 | 25 | 75 |
| Oleate | 2 | 75 | 20 | 77 |

<sup>a</sup>Reaction conditions: Glycerol/MethylEster molar relation of 6, 4% in weight of catalyst with regard to total mass of reactives, 220° C.

The invention claimed is:

1. A procedure for obtaining fatty acid monoesters and polyhydroxylic alcohols by transesterification between a polyhydroxylic alcohol and a compound selected from a fat of animal origin, a fat of vegetable origin and a fatty acid methyl ester, wherein the transesterification reaction is performed in the presence of basic solid catalysts, said solids being oxides selected from:
   mixed oxides of one or more monovalent metals and one or more trivalent metals,
   mixed oxides of one or more divalent metals and one or more trivalent metals which are one or more hydrated mixed oxides of one or more trivalent metals $M^{III}$ and one or more divalent metals $M^{II}$, and mixtures of same, with a $M^{II}/M^{III}$ ratio of between 2 and 5, the water content of these hydrated mixed oxides being between 15 and 80% by weight with respect to the precursor mixed oxide,
   and mixtures of same.

2. The procedure for obtaining fatty acid monoesters and polyhydroxylic alcohols according to claim 1, wherein the catalysts comprises mixed oxides of one or more trivalent metals $M^{III}$, and one or more monovalent metals $M^{I}$, and mixtures of same, for which the ratio $M^{I}/M^{III}$ is between 2 and 4.

3. The procedure for obtaining fatty acid monoesters and polyhydroxylic alcohols according to claim 2, wherein said trivalent metal is selected from Ga, Al, Fe, B, Ce, La and mixtures of same.

4. The procedure for obtaining fatty acid monoesters and polyhydroxylic alcohols according to claim 2, wherein said monovalent metal is selected from the group consisting of Li, Na, K, Rb, Cs and mixtures of same.

5. The procedure for obtaining fatty acid monoesters and polyhydroxylic alcohols according to claim 2, wherein said divalent metal is selected from the group consisting of Mg, Zn, Co, Ni, Ca, Cu, Mn and mixtures of same.

6. The procedure for obtaining fatty acid monoesters and polyhydroxylic alcohols according to claim 2, wherein the catalyst is alumina impregnated with salts which, after its calcination, produces the corresponding oxide supported on the alumina and in which the percentage of the impregnated salt is between 1 and 40%.

7. The procedure for obtaining fatty acid monoesters and polyhydroxylic alcohols according to claim 6, wherein said impregnated salts are selected from the group consisting of organic salts, nitrates, carbonates and hydroxides of alkaline metals selected from the group consisting of Li, Na, K, Rb, Cs and mixtures of same.

8. The procedure for obtaining fatty acid monoesters and polyhydroxylic alcohols according to claim 1 wherein said catalyst is a mixed oxide selected from the group consisting of mixed oxide of aluminium and magnesium, mixed oxide of aluminium and lithium, and mixed oxide impregnated on gamma-alumina.

9. The procedure for obtaining fatty acid monoesters and polyhydroxylic alcohols according to claim 1 wherein said fats are triglycerides selected from the group consisting of fish oil, coconut oil, palm oil, corn oil, olive oil, soya oil and rapeseed oil.

10. The procedure for obtaining fatty acid monoesters and polyhydroxylic alcohols according to claim 1 wherein said methyl esters are esters of fatty acids, saturated or unsaturated, which contain between 10 and 32 carbon atoms.

11. The procedure for obtaining fatty acid monoesters and polyhydroxylic alcohols according to claim 1 wherein said polyhydroxylic alcohols selected from the group consisting of glycerol, polyethylene glycols, sorbitol, mannitol and xylitol.

12. The procedure for obtaining fatty acid monoesters and polyhydroxylic alcohols according to claim 1 wherein the transesterification reaction is performed in a temperature range of between 50 and 260° C., using a proportional weight of polyol/ester between 0.2 and 20, the quantity of catalyst used being between 0.1 and 10% with respect to the total weight of reagents.

13. The procedure for obtaining fatty acid monoesters and polyhydroxylic alcohols according to claim 1 wherein the reaction is performed in the presence of air or in an inert atmosphere, at a pressure selected from atmospheric pressure, reduced pressure between 10 to 100 mmHg and at a pressure of between 2 and 100 atm.

* * * * *